(12) United States Patent
Ditrich et al.

(10) Patent No.: US 11,639,358 B2
(45) Date of Patent: May 2, 2023

(54) PROCESS FOR PREPARING AN OPTICALLY ACTIVE CINEOLE DERIVATIVE

(71) Applicant: BASF Agro B.V., Arnhem (NL)

(72) Inventors: Klaus Ditrich, Ludwigshafen (DE); Michael Rack, Ludwigshafen (DE); Stefan Benson, Ludwigshafen (DE); Roland Goetz, Ludwigshafen (DE); Helmut Kraus, Research Triangle Park, NC (US)

(73) Assignee: BASF AGRO B.V., Arnhem (NL)

( * ) Notice: Subject to any disclaimer, the term of this patent is extended or adjusted under 35 U.S.C. 154(b) by 493 days.

(21) Appl. No.: 16/614,163

(22) PCT Filed: May 9, 2018

(86) PCT No.: PCT/EP2018/062039
§ 371 (c)(1),
(2) Date: Nov. 15, 2019

(87) PCT Pub. No.: WO2018/210662
PCT Pub. Date: Nov. 22, 2018

(65) Prior Publication Data
US 2022/0033411 A1    Feb. 3, 2022

(30) Foreign Application Priority Data
May 19, 2017  (EP) ..................................... 17171868

(51) Int. Cl.
*C07D 493/08*    (2006.01)

(52) U.S. Cl.
CPC ........ *C07D 493/08* (2013.01); *C07B 2200/07* (2013.01)

(58) Field of Classification Search
CPC .......................... C07D 493/08; C07B 2200/07
See application file for complete search history.

(56) References Cited

U.S. PATENT DOCUMENTS

| | | | | |
|---|---|---|---|---|
| 4,487,945 A | * | 12/1984 | Payne | C07C 29/106 549/463 |
| 5,726,344 A | * | 3/1998 | West | C07C 69/013 560/194 |

OTHER PUBLICATIONS

Recrystallization ((file:///C:/Users/smoore2/Downloads/Recrystallization%20(1).pdf, downloaded Apr. 24, 2021, pp. 1-18).*
Qian et al. (Environ. Sci. Technol., 2011, 45, pp. 7036-7043).*

* cited by examiner

*Primary Examiner* — Susanna Moore
(74) *Attorney, Agent, or Firm* — Marshall, Gerstein & Borun LLP

(57) ABSTRACT

The present invention relates to a process for preparing optically active 1,4-cineole derivatives by enzymatic resolution and enantiomerically pure optically active 1,4-cineole derivatives of purity greater than 99.9% that have been prepared by this process. The present invention further relates to a process for preparing 7-oxabicyclo[2.2.1]heptane derivatives from the enantiomerically pure optically active 1,4-cineole derivatives.

19 Claims, No Drawings

PROCESS FOR PREPARING AN OPTICALLY ACTIVE CINEOLE DERIVATIVE

This application is a National Stage application of International Application No. PCT/EP2018/062039 filed May 9, 2018. This application also claims priority under 35 U.S.C. § 119 to European Patent Application No. 17171868.7, filed May 19, 2017.

FIELD OF THE INVENTION

The present invention relates to a process for preparing optically active 1,4-cineole derivatives by enzymatic resolution and enantiomerically pure optically active 1,4-cineole derivatives of purity greater than 99.9% that have been prepared by this process. The present invention further relates to a process for preparing 7-oxabicyclo[2.2.1]heptane derivatives from the enantiomerically pure optically active 1,4-cineole derivatives.

BACKGROUND OF THE INVENTION

Cinmethylin is a herbicide which inhibits tyrosine metabolism and such prevents the plant from producing plastoquinones and tocopherols. Cinmethylin is racemic (±)-2-exo-(o-methyl benzyl ether)-1,4-cineole. It was introduced as a racemate by Shell in 1989.

The racemic mixture contains equal parts of two enantiomers (+)-2-exo-(2-methylbenzyloxy)-1-methyl-4-isopropyl-7-oxabicyclo[2.2.1]heptane (CAS-No. 87818-61-9) and (−)-2-exo-(2-methylbenzyloxy)-1-methyl-4-isopropyl-7-oxabicyclo[2.2.1]heptane (CAS-No. 87819-60-1). The exo-(±)-isomers, the exo-(+)-isomer and the exo-(−)isomers including their preparation and herbicidal properties are disclosed in EP 0,081,893 (refer examples 29, 34, 35 and 62). Further preparation methods of these compounds are described in U.S. Pat. No. 4,487,945 (see embodiments 46 and 48), which comprises cyclising the corresponding cis 3,4-epoxycyclohexanol by treatment with an acid. The racemic mixture (±)2-exo-(2-methylbenzyloxy)-1-methyl-4-isopropyl-7-oxabicyclo[2.2.1]heptane is also described in the "The Pesticide Manual, Fourteenth Edition, Editor: C. D. S. Tomlin, British Crop Production Council, 2006, entry 157, pages 195-196 with its common name cinmethylin, its IUPAC name (1RS,2SR,4SR)-1,4-epoxy-p-meth-2-yl 2-methylbenzyl ether and its chemical abstract name exo-(±)-1-methyl-4-(1-methylethyl)-2-[(2-methylphenyl) methoxy]-7-oxabicyclo[2.2.1]heptane.

J. Chem. Soc. (c), 1969, pages 716-721, reports a process for the preparation of 2-endo-hydroxy-1-methyl-4-isopropyl-7-oxabicyclo[2,2,1]heptane.

2-Exo-hydroxy-1,4-cineole is a key synthetic intermediate and it may be made by the epoxidation of 1,4-terpinen-4-ol followed by acid catalyzed rearrangement. Alternatively, 1,4-cineole is hydroxylated by using the microorganisms to produce 2-exo-hydroxy-1,4-cineole. Hydroxylation at the 2-position was the most commonly observed microbial transformation although hydroxylation at carbons 3 and 8 were also observed in addition to the formation of 2-oxocineole. In addition to the formation of specific 2-hydroxycineole isomers from the enantiomeric 2-oxo-1,4-cineoles, with the potential for synthesis of specific cinmethylin isomers, can be achieved by making use of strains of *Curvularia lunata* and *Penicillium frequentans* (Refer Appl. Environ. Microbiol. 53: 2482 (1987) by Rosazza J P N, Steffens J J, Sariaslani S. Goswami A., Beale J M, Reeg S., Chapman R.).

One of its syntheses starts from commercially available terpinen-4-ol, a compound found in essential oils. As terpinen-4-ol is isolated from natural sources, it is available as a racemate as well as in enantio-enriched mixtures. In this established cinmethylin synthesis, terpinen-4-ol (1) is epoxidized in a metal (vanadium) directed epoxidation to an intermediate epoxide (2) which is subjected to an acid catalyzed epoxide opening, yielding the hydroxy-cineol (3). As both steps occur with perfect retention of the stereocenters and the final benzylation of (3) is also stereoretentative, the enantiomeric purity of the starting material (1) is reflected in the final cinmethylin product (4). A summary of the standard synthesis is outlined below:

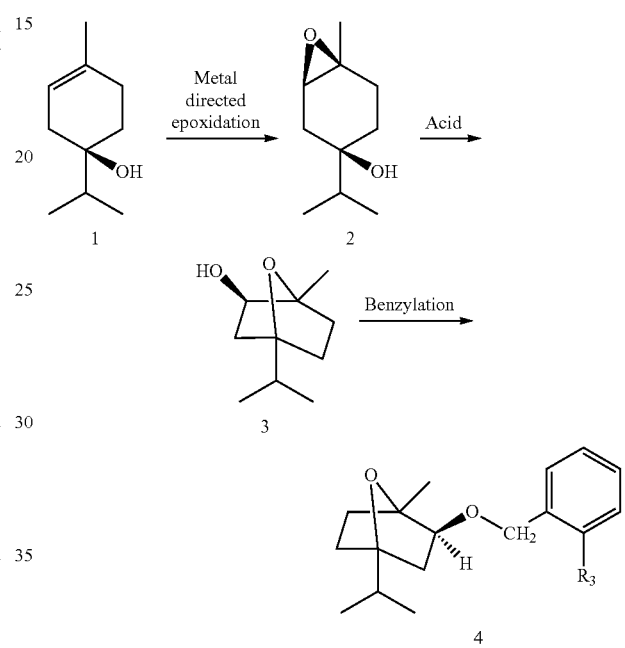

As the epoxidation and acid catalyzed rearrangement occurs in a stereoselective manner, the final product, cinmethylin, is obtained in a non-racemic form when the starting material is nonracemic.

In enantioselective syntheses, there is always a loss of precious material. To avoid losses of precious material, it is economic to do a racemate resolution in an early phase of a multi-step synthesis. Therefore, there is a need to investigate about the possibility to resolve the enantiomers of (3) by an enzyme-catalyzed kinetic resolution of one enantiomer of terpinen-4-ol (1) or hydroxy-cineol (3).

Moreover, the published processes proceed with poor yields, and the optical purity is still not satisfactory either.

It is well-known from the literature that enantiomers of cinmethylin show differences in herbicidal activity (Ref: U.S. Pat. No. 4,487,945; column 8, paragraph 15-25). The enantiomeric excess plays a very important role in herbicidal activity.

Thus, there is a need to develop an efficient process for preparing optically active 1,4-cineole derivatives and 7-oxabicyclo[2.2.1]heptane derivatives by the enzymatic resolution with excellent enantiomeric excess without compromising good yield.

OBJECTIVES OF THE INVENTION

The main objective of the invention is to provide a process for obtaining enantiomerically pure 1,4-cineole derivatives by the enantioselective enzymatic resolution with excellent enantiomeric excess without compromising yield.

Another objective of the invention is to provide a process for obtaining enantiomerically pure 7-oxabicyclo[2.2.1]heptane derivatives from the enantiomerically pure optically active 1,4-cineole derivatives with excellent enantiomeric excess without compromising yield.

Yet another objective of the invention is to provide a process for obtaining enantiomerically pure 7-oxabicyclo [2.2.1]heptane derivatives which avoid loss of precious material by carrying out the enantioselective enzymatic resolution in an early phase of a multi-step synthesis.

Yet another objective of the invention is to provide enantiomerically pure 1,4-cineole derivatives with enantiomeric excess of greater than 99.5% purity.

Yet another objective of the invention is to provide enantiomerically pure 7-oxabicyclo[2.2.1]heptane derivatives with enantiomeric excess of greater than 99.9% purity.

Yet another objective of the invention is to provide a simple process of preferential crystallization to obtain enantiomerically enriched 1,4-cineol derivatives.

SUMMARY OF THE INVENTION

It has now been found that, surprisingly, optically active cineole derivatives of formulae (II-R), (II-S), (IIa-R) and (IIa-S) can be obtained when an enantiomer mixture is acylated enantioselectively in the presence of a hydrolase enzyme. The unacylated derivate has been separated and the same can be recycled in the process and the loss of the precious material is eliminated. The optically active enantiomer so obtained has an enantiomeric excess of at least 70 to 87% ee. The enantiomeric excess surprisingly could be further enhanced to greater than 99.9% ee by simple preferential crystallization method. Further, said optically active cineole derivative with enantiomeric excess greater than 99.9% can be used to prepare optically active 7-oxabicyclo [2.2.1]heptane derivatives with enantiomeric excess of at least 99.9% purity without compromising yield.

Accordingly, in one embodiment, the presently claimed invention is directed to a process for preparing an optically active compound of formula (II-R),

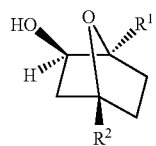

formula (II-R)

or an optically active compound of formula (II-S),

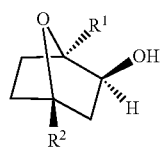

formula (II-S)

wherein
R$^1$ is selected from hydrogen and unsubstituted or substituted alkyl and
R$^2$ is selected from hydrogen and unsubstituted or substituted alkyl;

said process comprises at least the steps of:
(i) reacting a mixture comprising a compound of formula (II)

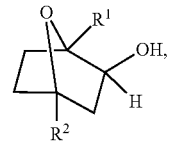

(II)

wherein R$^1$ and R$^2$ are as defined above, with an acylating agent in the presence of a hydrolase to obtain a mixture containing the first enantiomer of the compounds of formula (II) in acylated form and the second enantiomer of the compounds of formula (II) in unacylated form; and (ii) isolating the second enantiomer of the compound of formula (II) in unacylated form from the mixture of step (i) to obtain an optically active compound of formula (II-R) or an optically active compound of formula (II-S) and a mixture containing the first enantiomer of the compounds of formula (II) in acylated form.

In another embodiment of the presently claimed invention, said process further comprises the steps of:
(iii) subjecting the mixture of step (ii) to basic saponification to obtain a mixture containing the first enantiomer of the compounds of formula (I) in unacylated form; and
(iv) isolating the first enantiomer of the compounds of formula (I) in unacylated form from the mixture of step (iii) to obtain an optically active compound of formula (II-R) or an optically active compound of formula (II-S).

In another embodiment of the presently claimed invention, said process further comprises the steps of:
v) Providing a suspension comprising the optically active enantiomers of formula (II-R) or formula (II-S) as obtained in step (iv) in at least one non-polar solvent;
vi) Stirring the suspension obtained in step (v) at temperature in the range of 10° C. to reflux temperature of the non-polar solvent; and
vii) Isolating the crystals of the optically active enantiomer of formula (II-R) or formula (II-S) obtained in step (vi).

In another embodiment of the presently claimed invention, said process further comprises adding seed crystals of the desired enantiomer of formula (II-R) or formula (II-S) in step (vi).

The term "desired" denotes the optically active enantiomer of formula (II-R) or formula (II-S) with enantiomeric excess of at least 99.5% ee, especially obtained in step (vi).

The term "seed" crystals denotes a small piece of single crystal/polycrystal of the desired enantiomer from which a large crystal of the same enantiomer typically is to be grown.

In another embodiment of the presently claimed invention, R$^1$ is selected from hydrogen and C$_1$-C$_6$-alkyl; wherein alkyl is straight-chain or branched, unsubstituted or substituted with 1, 2, 3, 4 or 5 substituents selected from the group consisting of F, Cl, Br, I, CN, NO$_2$, methyl, phenyl and benzyl; and R$^2$ is selected from hydrogen and C$_1$-C$_6$-alkyl; wherein alkyl is straight-chain or branched, unsubstituted or substituted with 1, 2, 3, 4 or 5 substituents selected from the group consisting of F, Cl, Br, I, CN, NO$_2$, methyl, phenyl and benzyl.

The term "straight-chain" denotes a chain of atoms with no side chain attached to it.

The term "branched" denotes a chain of atoms with one or more side chains attached to it. Branching occurs by the replacement of a substituent, e.g. a hydrogen atom, with a covalently bonded alkyl radical.

"Alkyl" denotes a moiety constituted solely of atoms of carbon and a hydrogen.

In another embodiment of the presently claimed invention, $R^1$ is methyl and $R^2$ is isopropyl.

In another embodiment of the presently claimed invention, in the mixture in step (i) (a) the first enantiomer of the compounds of formula (II) in acylated form is the optically active compound of formula (II-S) and the second enantiomer of the compounds of formula (II) in unacylated form is the optically active compound of formula (II-R); or (b) the first enantiomer of the compounds of formula (II) in acylated form is the optically active compound of formula (II-R) and the second enantiomer of the compounds of formula (II) in unacylated form is the optically active compound of formula (II-S).

In another embodiment of the presently claimed invention, the acylating agent is selected from the group consisting of a vinyl or propenyl ester of a saturated aliphatic carboxylic acid, aliphatic alkyl ester of a saturated cycloaliphatic carboxylic acid and saturated aliphatic carboxylic acid anhydrides. Preferably the vinyl or propenyl ester of a saturated aliphatic carboxylic acid is selected from the group consisting of vinyl acetate, vinyl propionate, vinyl butyrate, vinyl pentanoate, vinyl decanoate, vinyl dodecanoate, propenyl acetate, propenyl propionate, propenyl butyrate, propenyl pentanoate, propenyl decanoate and propenyl dodecanoate. Preferably the saturated aliphatic carboxylic acid anhydride is selected from the group consisting of succinic anhydride, acetic anhydride, propionic anhydride, butyric anhydride, pentanoic anhydride, decanoic anhydride, and dodecanoic anhydride.

In another embodiment of the presently claimed invention, the acylating agent is either vinyl dodecanoate or succinic anhydride.

In another embodiment of the presently claimed invention, the hydrolase is selected from the group consisting of lipases from bacteria of the *Burkholderia* genera, lipases from bacteria of the *Pseudomonas* genera, lipases from fungal strains of *Thermomyces* and yeasts from the *Candida* genus.

In another embodiment of the presently claimed invention, the hydrolase is immobilized on a solid support selected from the group consisting of activated carbon; silicon dioxide; sulfates of alkali and alkaline earth metals, carbonates of alkali and alkaline earth metals, synthetic polymers, and anion exchange materials and clays. Preferably sulfates of alkali and alkaline earth metals are selected from the group consisting of sodium sulfate, magnesium sulfate, calcium sulfate and barium sulfate. Preferably carbonates of alkali and alkaline earth metals are selected from the group consisting of sodium carbonate, magnesium carbonate, calcium carbonate and barium carbonate. Preferably synthetic polymers are selected from the group consisting of polystyrene, acrylic resins, phenol-formaldehyde resins polyolefins and polyurethanes. Preferably polyolefins are selected from the group consisting of polyethylene and polypropylene.

In another embodiment of the presently claimed invention, in step (i) the compound of formula (II) and the acylating agent is reacted in an organic solvent selected from the group consisting of group consisting of ethers, halogenated hydrocarbons; and aliphatic, cyclic and aromatic hydrocarbon solvents. Preferably, the ethers are selected from the group consisting of diethyl ether, dipropyl ether, diisopropyl ether, dibutyl ether, methyl tertiary butyl ether, ethyl tertiary butyl ether, tetrahydrofuran and dioxane. Preferably the halogenated hydrocarbons are selected from the group consisting of dichloromethane, chloroform, carbon tetrachloride, dichloroethane, tetrachloroethane, chlorobenzene and dichlorobenzene. Preferably aliphatic, cyclic and aromatic hydrocarbon solvents are selected from the group consisting of pentane, hexane, cyclopentane, cyclohexane, heptane, octane, cyclooctane, benzene, xylene and toluene.

More preferably, in step (i) the organic solvent used is methyl tertiary butyl ether.

In another embodiment of the presently claimed invention, in step (i) the compound of formula (II) and the acylating agent is reacted for a period of 30 minutes to 100 hours at a temperature in the range of $\geq 0$ to $\leq 70°$ C.

In another embodiment of the presently claimed invention, an excess of acylating agent is removed before step (ii).

In another embodiment of the presently claimed invention, in step (ii) the second enantiomer of the compound of formula (II) in unacylated form is isolated from the mixture containing the first enantiomer of the compounds of formula (II) in acylated form and the second enantiomer of the compounds of formula (II) in unacylated form by subjecting the mixture to a distillation or a sublimation at a pressure in the range 10 to 500 Pa and a temperature in the range of 20 to 240° C.

In another embodiment of the presently claimed invention, in step (ii) the second enantiomer of the compound of formula (II) in unacylated form is isolated from the mixture containing the first enantiomer of the compounds of formula (II) in acylated form and the second enantiomer of the compounds of formula (II) in unacylated form by subjecting the mixture to an extraction in which the pH of the aqueous phase is adjusted to pH 7 and by addition of a base. The first enantiomer in acylated form is extracted into the aqueous phase leaving second enantiomer in unacylated form in the organic phase.

In another embodiment of the presently claimed invention, in step (ii) the base is selected from sodium carbonate, sodium bicarbonate, ammonium hydroxide, sodium hydroxide, and potassium hydroxide.

In another embodiment of the presently claimed invention, in step (iii) the basic conditions are obtained by using an inorganic base in a polar solvent.

In another embodiment of the presently claimed invention, the polar solvent is selected from the group consisting of alcohol and water. Preferably the alcohols are selected from the group consisting of methanol, ethanol, n-propanol, n-butanol, iso-butanol, and amyl alcohol.

In another embodiment of the presently claimed invention, in step (v) the suspension is stirred at temperature in the range of $\geq 10$ to $\leq 120°$ C., preferably $\geq 20$ to $\leq 115°$ C.

In another embodiment of the presently claimed invention, in step (vii) the isolation of the crystals of the desired enantiomer is carried out at temperature in the range of $\geq -10$ to $\leq 30°$ C., preferably $\geq 10$ to $\leq 25°$ C.

In another embodiment of the presently claimed invention, in step (vii) the desired enantiomer is isolated by a method selected from the group consisting of filtration or evaporation.

In another embodiment of the presently claimed invention, in step (v) the non-polar solvent is a solvent having polarity index $\geq 0.0$ to $\leq 4.0$.

In another embodiment of the presently claimed invention, in step (v) the non-polar solvent is a hydrocarbon.

In another embodiment of the presently claimed invention, in step (v) the non-polar solvent is a hydrocarbon having polarity index of ≥0.0 to ≤2.5.

In another embodiment of the presently claimed invention, the hydrocarbon is selected from the group consisting of petroleum ether, pentane, cyclopentane, hexane, cyclohexane, heptane, n-octane, iso-octane, cyclooctane, benzene, xylene and toluene.

Accordingly, in another embodiment, the presently claimed invention is directed to an optically active compound of formula (IIa-R),

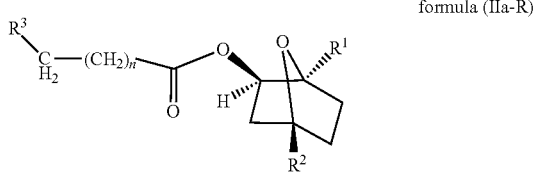

formula (IIa-R)

or an optically active compound of formula (IIa-S),

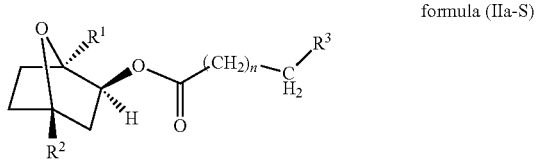

formula (IIa-S)

wherein
$R^1$ is selected from hydrogen and unsubstituted or substituted alkyl;
$R^2$ is selected from hydrogen and unsubstituted or substituted alkyl;
$R^3$ is selected from hydrogen and —COOR'; wherein R' is hydrogen or unsubstituted or substituted alkyl; and
n is 1 to 16.

In another embodiment of the presently claimed invention, in the compounds of formulae (IIa-R) and (IIa-S), $R^1$ is selected from hydrogen and $C_1$-$C_6$-alkyl; wherein alkyl is straight-chain or branched, unsubstituted or substituted with 1, 2, 3, 4 or 5 substituents selected from the group consisting of F, Cl, Br, I, CN, $NO_2$, methyl, phenyl and benzyl; $R^2$ is selected from hydrogen and $C_1$-$C_6$-alkyl; wherein alkyl is straight-chain or branched, unsubstituted or substituted with 1, 2, 3, 4 or 5 substituents selected from the group consisting of F, Cl, Br, I, CN, $NO_2$, methyl, phenyl and benzyl; $R^3$ is selected from hydrogen and —COOR'; wherein R' is hydrogen or $C_1$-$C_6$-alkyl; wherein alkyl is straight-chain or branched, unsubstituted or substituted with 1, 2, 3, 4 or 5 substituents selected from the group consisting of F, Cl, Br, I, CN, $NO_2$, methyl, phenyl and benzyl; and n is 1 to 10.

In another embodiment of the presently claimed invention, in the compounds of formulae (IIa-R) and (IIa-S), $R^1$ is methyl; $R^2$ is isopropyl; $R^3$ is hydrogen or —COOH; and n is 10 or 1.

In another embodiment of the presently claimed invention, in the compounds of formulae (IIa-R) and (IIa-S), $R^1$ is methyl; $R^2$ is isopropyl; $R^3$ is hydrogen; and n is 10.

In another embodiment of the presently claimed invention, the optically active compound of formula (IIa-R) is [(1R,2S,4S)-4-isopropyl-1-methyl-7-oxabicyclo[2.2.1]heptan-2-yl]dodecanoate and the optically active compound of formula (IIa-S) is [(1S,2R,4R)-4-isopropyl-1-methyl-7-oxabicyclo[2.2.1]heptan-2-yl]dodecanoate.

In another embodiment of the presently claimed invention, in the compounds of formulae (IIa-R) and (IIa-S), $R^1$ is methyl; $R^2$ is isopropyl; $R^3$ is —COOH; and n is 1.

In another embodiment of the presently claimed invention, the optically active compound of formula (IIa-R) is 4-[[(1R,2S,4S)-4-isopropyl-1-methyl-7-oxabicyclo[2.2.1]heptan-2-yl]oxy]-4-oxo-butanoic acid and the optically active compound of formula (IIa-S) is 4-[[(1S,2R,4R)-4-isopropyl-1-methyl-7-oxabicyclo[2.2.1]heptan-2-yl]oxy]-4-oxo-butanoic acid.

Accordingly, in another embodiment, the presently claimed invention is directed to a process for preparing an optically active compound of formula (I-R),

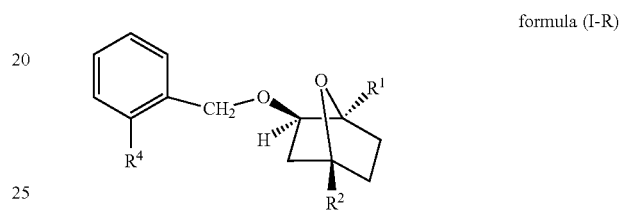

formula (I-R)

or optically active compounds of formula (I-S),

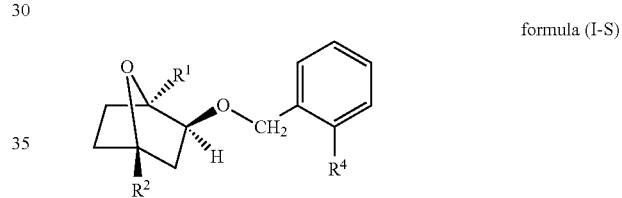

formula (I-S)

wherein
$R^1$ is selected from hydrogen and unsubstituted or substituted alkyl;
$R^2$ is selected from hydrogen and unsubstituted or substituted alkyl; and
$R^4$ is unsubstituted or substituted alkyl;
by reacting an optically active compound of formula (II-R) obtained according to the process as described above or an optically active compound of formula (II-S) obtained according to the process as described above in the presence of a non-polar solvent and in the presence of a base with a compound of formula (III),

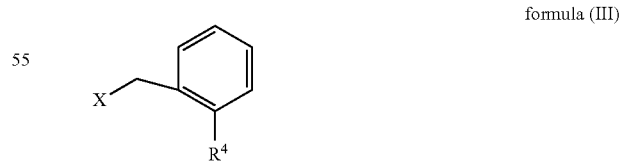

formula (III)

wherein X is a leaving group and $R^4$ is unsubstituted or substituted alkyl.

The term "leaving group" as used herein refers to any group that departs the molecule with a pair of electrons in heterolytic bond cleavage such that the molecule is capable of participating in the nucleophilic substitution reaction of the process of this invention.

In another embodiment of the presently claimed invention, the leaving group X is selected from the group consisting of halogen, an oxygen linked leaving group, an ammonium group of formula (IV);

$$—N(R'_1)(R'_2)(R'_3)^+Y^- \quad (IV)$$

wherein $R'_1$, $R'_2$ and $R'_3$ are each independently selected from $C_1$-$C_6$-alkyl, $C_3$-$C_{10}$-cycloalkyl and $C_6$-$C_{20}$-aryl, and $Y^-$ is selected from halide, hydroxide, $C_1$-$C_4$-alkyl sulfonate and $C_6$-$C_{20}$-aryl sulfonate ions.

In another embodiment of the presently claimed invention, halogen is selected from a chlorine, a bromine, an iodine and a fluorine.

In another embodiment of the presently claimed invention, oxygen linked leaving groups are selected from group consisting of $C_1$-$C_4$-alkyl sulfonates, $C_1$-$C_4$-haloalkyl sulfonates, $C_6$-$C_{20}$-aryl sulfonates, $C_3$-$C_{10}$-cycloalkyl sulfonates and imidazolylsulfonate (imidazylate), more preferably from $C_1$-$C_4$-alkyl sulfonates, $C_1$-$C_4$-haloalkyl sulfonates and $C_6$-$C_{20}$-aryl sulfonates and even more preferably from $C_1$-$C_4$-alkyl sulfonates and $C_6$-$C_{20}$-aryl sulfonates.

Examples of $C_1$-$C_4$-alkyl sulfonates include but are not limited to mesylate (methanesulfonate), esylate (ethanesulfonate), n-propylsulfonate, iso-propylsulfonate, n-butylsulfonate, iso-butylsulfonate, sec-butylsulfonate and tert-butylsulfonate.

Examples of $C_1$-$C_4$-haloalkyl sulfonates include but are not limited to triflate (trifluoromethanesulfonate) and trichloromethanesulfonate.

Examples of $C_3$-$C_{10}$-cycloalkyl sulfonates include but are not limited to cyclohexylsulfonate.

Examples of $C_6$-$C_{20}$-aryl sulfonates include but are not limited to tosylate (p-toluenesulfonate), besylate (benzenesulfonate) and 2-naphtyl sulfonate.

In another embodiment of the presently claimed invention, the oxygen linked leaving group is selected from mesylate (methanesulfonate), esylate (ethanesulfonate), n-propylsulfonate, isopropylsulfonate, n-butylsulfonate, iso-butylsulfonate, sec-butylsulfonate, tert-butylsulfonate, triflate (trifluoromethanesulfonate), trichloromethanesulfonate, tosylate (p-toluenesulfonate), besylate (benzenesulfonate), 2-naphtyl sulfonate, cyclohexylsulfonate and imidazolylsulfonate (imidazylate), more preferably from mesylate, esylate, triflate, tosylate and besylate and even more preferably from mesylate and tosylate.

In another embodiment of the presently claimed invention, ammonium group of formula (IV)

$$N(R'_1)(R'_2)(R'_3)+Y^- \quad (IV)$$

wherein $R'_1$, $R'_2$, and $R'_3$ are each independently selected from $C_1$-$C_6$-alkyl and $Y^-$ is selected from halide, hydroxide, $C_1$-$C_4$-alkyl sulfonate and $C_6$-$C_{20}$-aryl sulfonate ions.

In another embodiment of the presently claimed invention, ammonium group of formula (IV) wherein $R'_1$, $R'_2$ and $R'_3$ are each independently selected from $C_1$-$C_6$-alkyl and $Y^-$ is selected from a chlorine, bromine, iodine, hydroxide, mesylate and tosylate ion.

Examples of ammonium group of formula (IV) include but are not limited to a trimethyl ammonium chloride group of formula (IVa);

$$—N(CH_3)_3^+Cl^- \quad (IVa),$$

and a triethyl ammonium chloride group of formula (IVb);

$$—N(CH_2CH_3)_3^+Cl^- \quad (IVb).$$

In another embodiment of the presently claimed invention, the leaving group X is preferably bromine.

In another embodiment of the presently claimed invention, in the compounds of formulae (I-R) and (I-S), $R^1$ is selected from hydrogen and $C_1$-$C_6$-alkyl; wherein alkyl is straight-chain or branched, unsubstituted or substituted with 1, 2, 3, 4 or 5 substituents selected from the group consisting of F, Cl, Br, I, CN, $NO_2$, methyl, phenyl and benzyl; $R^2$ is selected from hydrogen and $C_1$-$C_6$-alkyl; wherein alkyl is straight-chain or branched, unsubstituted or substituted with 1, 2, 3, 4 or 5 substituents selected from the group consisting of F, Cl, Br, I, CN, $NO_2$, methyl, phenyl and benzyl; and $R^4$ is selected from $C_1$-$C_6$-alkyl; wherein alkyl is straight-chain or branched, unsubstituted or substituted with 1, 2, 3, 4 or 5 substituents selected from the group consisting of F, Cl, Br, I, CN, $NO_2$, methyl, phenyl and benzyl.

In another embodiment of the presently claimed invention, the non-polar solvent is a hydrocarbon selected from the group consisting of pentane, hexane, cyclopentane, cyclohexane, heptane, octane, cyclooctane, benzene, xylene and toluene.

Accordingly, in another embodiment, the presently claimed invention is directed to an optically active compound of formula (I-R) and (I-S) selected from the group consisting of (1R,2S,4S)-4-isopropyl-1-methyl-2-(o-tolylmethoxy)-7-oxabicyclo[2.2.1]heptane and (1S,2R,4R)-4-isopropyl-1-methyl-2-(o-tolyl methoxy)-7-oxabicyclo[2.2.1]heptane.

DETAILED DESCRIPTION OF THE INVENTION

For the purposes of promoting an understanding of the principles of the invention, specific language will be used to describe exemplary embodiments of the present invention. It will nevertheless be understood that no limitation of the scope of the invention is thereby intended. The invention includes any alterations and further modifications in the described methods and described optically active compounds of the principles of the invention which would normally occur to one skilled in the art to which the invention relates.

The present invention provides methods for producing enantiomerically enriched said optically active compounds, utilizing stereoselective enzymes for preferential acylation or preferential hydrolysis of one of the enantiomers of said optically active compounds, followed by the isolation of a specific enantiomer.

The stereoselectivity of acylation or hydrolysis originates from the specific character of location of functional groups within the active centre of the enzyme molecule, which favors binding of one stereo-form of the substrate over the other form and provides for higher reactivity of this stereo-form in the acylation or hydrolysis reaction.

The invention therefore relates to a process for enantioselectively acylating 1,4-cineole derivatives of formula (II) to obtain the optically active compounds of formula (II-R) or the optically active compounds of formula (II-S). In said process, the mixture comprising compound of formula (II) is reacted with an acylating agent in the presence of a hydrolase in step (i) to obtain a mixture in which one enantiomer is present essentially in the acylated form and the other enantiomer is present essentially in the unacylated form. In step (ii), the second enantiomer of the compound of formula (II) in unacylated form is isolated from the mixture of step (i) to obtain an optically active compound of formula (II-R) or an optically active compound of formula (II-S) and a mixture containing the first enantiomer of the compounds of formula (II) in acylated form. The process further comprises the step (iii) in which the mixture so obtained in step (ii) is subjected to basic saponification to obtain a mixture containing the first enantiomer of the compounds of formula (I) in unacylated form. In step (iv), the first enantiomer of the compounds of formula (I) in unacylated form is isolated from the mixture of step (iii) to obtain an optically active compound of formula (II-R) or an optically active compound of formula (II-S).

The mixture of step (i) comprises (a) the first enantiomer of the compounds of formula (II) in acylated form is the optically active compound of formula (II-S) and the second enantiomer of the compounds of formula (II) in unacylated form is the optically active compound of formula (II-R); or (b) the first enantiomer of the compounds of formula (II) in acylated form is the optically active compound of formula (II-R) and the second enantiomer of the compounds of formula (II) in unacylated form is the optically active compound of formula (II-S).

The remarks made below regarding preferred embodiments of the process according to the presently claimed invention, of the reactants and of the products apply both taken alone and especially in combination with one another.

Essentially, the acylating agent used in step (i) is selected from the group consisting of a vinyl or propenyl ester of a saturated aliphatic carboxylic acid selected from the group consisting of vinyl acetate, vinyl propionate, vinyl butyrate, vinyl pentanoate, vinyl decanoate, vinyl dodecanoate, propenyl acetate, propenyl propionate, propenyl butyrate, propenyl pentanoate, propenyl decanoate and propenyl dodecanoate; and saturated aliphatic carboxylic acid anhydride selected from the group consisting of succinic anhydride, acetic anhydride, propionic anhydride, butyric anhydride, pentanoic anhydride, decanoic anhydride, and dodecanoic anhydride.

The preferred acylating agents are either vinyl dodecanoate or succinic anhydride.

In the reaction in step (i), preference is given to using from 1 to 5 molar equivalents, more preferably from 1 to 4 molar equivalents and in particular from 1 to 3 molar equivalents of the acylating agent, based on the content of enantiomer of the compound of formula (II) which is acylated. Molar equivalents shall be understood to mean the number of carboxyl groups of the acylating agent in moles which can react with 1 mol of that enantiomer of the compound (II) which is acylated.

Essentially enantiomerically pure compounds of formulae (II-S) and (II-R) should be understood in the context of the present invention to mean that they are present in an enantiomeric purity of in each case at least 85% ee, preferably at least 95% ee and in particular at least 99.5% ee.

In step (i), preference is given to obtaining a mixture in which the R-enantiomer is present essentially in unacylated form and the S-enantiomer is present in essentially acylated form.

The hydrolase used in step (i) is preferably a protease and especially a lipase. This brings about a selective O-acylation of only one of the two enantiomers of compound (II). It preferably brings about the selective acylation of the (S) enantiomer of compound (II). The hydrolase is preferably obtained from a microorganism, more preferably from a bacterium or a yeast. Likewise, suitable are hydrolases which are obtainable by recombinant processes. The hydrolase can be used in purified or partly purified form or in the form of the microorganism itself. Processes for obtaining and purifying hydrolases from microorganisms are sufficiently well known to those skilled in the art, for example from EP-A-11149849 or EP-A-1069183. Preference is given to using the hydrolase in purified form.

The hydrolase may be used in free (i.e. in native form) or immobilized form. An immobilized enzyme is understood to mean an enzyme which is fixed to an inert support. Suitable support materials and the enzymes immobilized thereto are known from EP-A-1149849, EP-A-1069183 and DE-A 100193773 and from the literature references cited therein. In this context, reference is made to the full disclosure of these documents. The suitable support materials include, for example, activated carbon; silicon dioxide; sulfates of alkali and alkaline earth metals, selected from the group consisting of sodium sulfate, magnesium sulfate, calcium sulfate and barium sulfate; carbonates of alkali and alkaline earth metals, selected from the group consisting of sodium carbonate, magnesium carbonate, calcium carbonate and barium carbonate; synthetic polymers, selected from the group consisting of polystyrene, acrylic resins, phenol-formaldehyde resins, polyurethanes and polyolefins selected from the group consisting of polyethylene and polypropylene; anion exchange materials and clays. To prepare the supported enzymes, the support materials are typically used in a finely divided, particulate form, preference being given to porous forms. The particle size of the support material is typically not more than 5 mm, in particular not more than 2 mm (sieve grade).

Preference is given to using lipases (triacylglycerolacylhydrolases; EC 3.1.1.3). Among these, preference is given to lipases which are obtained from bacteria of the *Burkholderia* genera or *Pseudomonas* genera or fungal strains of *Thermomyces* or from yeasts of the *Candida* genus.

Examples of *Burkholderia* species are *Burkholderia ambifaria* (e.g. strains ATCC BAA-244, CCUG 44356, LMG 19182); *Burkholderia andropogonis* (e.g. strains ATCC 23061, CCUG 32772, CFBP 2421, CIP 105771, DSM 9511, ICMP 2807, JCM 10487, LMG 2129, NCPPB 934, NRRL B-14296); *Burkholderia caledonica* (e.g. strains W50D, CCUG 42236, CIP 107098, LMG 19076); *Burkholderia caribensis* (e.g. strains MWAP 64, CCUG 42847, CIP 106784, DSM 13236, LMG 18531); *Burkholderia caryophylli* (e.g. strains ATCC 25418, CCUG 20834, CFBP 2429, CFBP 3818, CIP 105770, DSM 50341, HAMBI 2159, ICMP 512, JCM 9310, JCM 10488, LMG 2155, NCPPB 2151); *Burkholderia cepacia* (e.g. strains Ballard 717, 717-ICPB 25, ATCC 25416, CCUG 12691, CCUG 13226, CFBP 2227, CIP 80.24, DSM 7288, HAMBI 1976, ICMP 5796, IFO 14074, JCM 5964, LMG 1222, NCCB 76047, NCPPB 2993, NCTC 10743, NRRL B-14810); *Burkholderia cocovenenans* (e.g. strains ATCC 33664, CFBP 4790, DSM 11318, JCM 10561, LMG 11626, NCIMB 9450); *Burkholderia fungorum* (e.g. strains Croize P763-2, CCUG 31961, CIP 107096, LMG 16225); *Burkholderia gladioli* (e.g. strains ATCC 10248, CCUG 1782, CFBP 2427, CIP 105410, DSM 4285, HAMBI 2157, ICMP 3950, IFO 13700, JCM 9311, LMG 2216, NCCB 38018, NCPPB 1891, NCTC 12378, NRRL B-793); *Burkholderia glathei* (e.g. strains ATCC 29195, CFBP 4791, CIP 105421, DSM 50014, JCM 10563, LMG 14190); *Burkholderia glumae* (e.g. strains ATCC 33617, CCUG 20835, CFBP 4900, CFBP 2430, CIP 106418, DSM 9512, ICMP 3655, LMG 2196, NCPPB 2981, NIAES 1169); *Burkholderia graminis* (e.g. strains C4D1M, ATCC 700544, CCUG 42231, CIP 106649, LMG 18924); *Burkholderia kururiensis* (e.g. strains KP 23, ATCC 700977, CIP 106643, DSM 13646, JCM 10599, LMG 19447); *Burkholderia mallei* (e.g. strains ATCC 23344, NCTC 12938); *Burkholderia multivorans* (e.g. strains ATCC BAA-247, CCUG 34080, CIP 105495, DSM 13243, LMG 13010, NCTC 13007); *Burkholderia norimbergensis* (e.g. strains R2, ATCC BAA-65, CCUG 39188, CFBP 4792, DSM 11628, CIP 105463, JCM 10565, LMG 18379); *Burkholderia phenazinium* (e.g. strains ATCC 33666, CCUG 20836, CFBP 4793, CIP 106502, DSM 10684, JCM 10564, LMG 2247, NCIB 11027); *Burkholderia pikettii* (e.g. strains ATCC 27511, CCUG 3318, CFBP 2459, CIP 73.23, DSM 6297, HAMBI 2158, JCM 5969, LMG 5942, NCTC 11149); *Burkholderia plantarii* (e.g. strains AZ 8201, ATCC 43733, CCUG 23368, CFBP 3573, CFBP 3997, CIP 105769, DSM 9509, ICMP 9424, JCM 5492, LMG 9035, NCPPB 3590, NIAES 1723); *Burkholderia pseudomallei* (e.g. strains WRAIR 286, ATCC 23343, NCTC 12939); *Burkholderia pyrrocinia* (e.g. strains ATCC 15958, CFBP 4794, CIP 105874, DSM 10685, LMG 14191); *Burkholderia sacchari* (e.g. strains CCT 6771, CIP 107211, IPT 101, LMG 19450); *Burkholderia solanacearum* (e.g. strains A. Kelman 60-1, ATCC 11696, CCUG 14272, CFBP 2047, CIP 104762, DSM 9544, ICMP 5712, JCM 10489, LMG 2299, NCAIM B.01459, NCPPB 325, NRRL B-3212); *Burkholderia stabilis* (e.g. strains ATCC BAA-67, CCUG 34168, CIP 106845, LMG 14294, NCTC 13011); *Burkholderia thailandensis* (e.g. strains E 264, ATCC 700388, CIP 106301, DSM 13276); *Burkholderia ubonensis* (e.g. strains EY 3383, CIP 107078, NCTC 13147); *Burkholderia vandii* (e.g. strains VA-1316, ATCC 51545, CFBP 4795, DSM 9510, JCM 7957, LMG 16020); *Burkholderia vietnamiensis* (e.g. strains TVV 75, ATCC BAA-248, CCUG 34169, CFBP 4796, CIP 105875, DSM 11319, JCM 10562, LMG 10929). Examples of *Pseudomonas* species are *Pseudomonas aeruginosa* (e.g. strains ATCC 10145, DSM 50071), *Pseudomonas agarici* (e.g. strains ATCC 25941, DSM 11810), *Pseudomonas alcaligenes* (e.g. strains ATCC 14909, DSM 50342), *Pseudomonas amygdali* (e.g. strains ATCC 337614, DSM 7298), *Pseudomonas anguiliseptica* (e.g. strains ATCC 33660, DSM 12111), *Pseudomonas antimicrobica* (e.g. strains DSM 8361, NCIB 9898, LMG 18920), *Pseudomonas aspleni* (e.g. strains ATCC 23835, CCUG 32773), *Pseudomonas aurantiaca* (e.g. strains ATCC 33663, CIP 106710), *Pseudomonas aureofaciens* (e.g. strains ATCC 13985, CFBP 2133), *Pseudomonas avellanae* (e.g. strains DSM 11809, NCPPB 3487), *Pseudomonas azotoformans* (e.g. strains CIP 106744, JCM 7733), *Pseudomonas balearica* (e.g. strains DSM 6083, CIP 105297), *Pseudomonas beijerinsckii* (e.g. strains ATCC 19372, DSM 6083), *Pseudomonas beteli* (e.g. strains ATCC 19861, CFBP 4337), *Pseudomonas boreopolis* (e.g. strains ATCC 33662, CIP 106717), *Pseudomonas carboxyhydrogena* (e.g. strains ATCC 29978, DSM 1083), *Pseudomonas caricapapayae* (e.g. strains ATCC 33615, CCUG 32775), *Pseudomonas cichorii* (e.g. strains ATCC 10857, DSM 50259), *Pseudomonas cissicola* (e.g. strains ATCC 33616, CCUG 18839), *Pseudomonas citronellolis* (e.g. strains ATCC 13674, DSM 50332), *Pseudomonas coronafaciens* (e.g. strains DSM 50261, DSM 50262), *Pseudomonas corrugata* (e.g. strains ATCC 29736, DSM 7228), *Pseudomonas doudoroffii* (e.g. strains ATCC 27123, DSM 7028), *Pseudomonas echinoides* (e.g. strains ATCC 14820, DSM 1805), *Pseudomonas elongata* (e.g. strains ATCC 10144, DSM 6810), *Pseudomonas ficuserectae* (e.g. strains ATCC 35104, CCUG 32779), *Pseudomonas flavescens* (e.g. strains ATCC 51555, DSM 12071), *Pseudomonas flectens* (e.g. strains ATCC 12775, CFBB 3281), *Pseudomonas fluorescens* (e.g. strains ATCC 13525, DSM 50090), *Pseudomonas fragi* (e.g. strains ATCC 4973, DSM 3456), *Pseudomonas fulva* (e.g. strains ATCC 31418, CIP 106765), *Pseudomonas fuscovaginae* (e.g. strains CCUG 32780, DSM 7231), *Pseudomonas gelidicola* (e.g. strains CIP 106748), *Pseudomonas geniculata* (e.g. strains ATCC 19374, LMG 2195), *Pseudomonas glathei* (e.g. strains ATCC 29195, DSM 50014), *Pseudomonas halophila* (e.g. strains ATCC 49241, DSM 3050), *Pseudomonas hibiscicola* (e.g. strains ATCC 19867, LMG 980), *Pseudomonas huttiensis* (e.g. strains ATCC 14670, DSM 10281), *Pseudomonas iners* (e.g. strain CIP 106746), *Pseudomonas lancelota* (e.g. strains ATCC 14669, CFBP 5587), *Pseudomonas lemoignei* (e.g. strains ATCC 17989, DSM 7445), *Pseudomonas lundensis* (e.g. strains ATCC 19968, DSM 6252), *Pseudomonas luteola* (e.g. strains ATCC 43273, DSM 6975), *Pseudomonas marginalis* (e.g. strains ATCC 10844, DSM 13124), *Pseudomonas meliae* (e.g. strains ATCC 33050, DSM 6759), *Pseudomonas mendocina* (e.g. strains ATCC 25411, DSM 50017), *Pseudomonas mucidolens* (e.g. strains ATCC 4685, CCUG 1424), *Pseudomonas monteilli* (e.g. strains ATCC 700476, DSM 14164), *Pseudomonas nautica* (e.g. strains ATCC 27132, DSM 50418), *Pseudomonas nitroreducens* (e.g. strains ATCC 33634, DSM 14399), *Pseudomonas oleovorans* (e.g. strains ATCC 8062, DSM 1045), *Pseudomonas oryzihabitans* (e.g. strains ATCC 43272, DSM 6835), *Pseudomonas pertucinogena* (e.g. strains ATCC 190, CCUG 7832), *Pseudomonas phenazinium* (e.g. strains ATCC 33666, DSM 10684), *Pseudomonas pictorum* (e.g. strains ATCC 23328, LMG 981), *Pseudomonas pseudoalcaligenes* (e.g. strains ATCC 17440, DSM 50188), *Pseudomonas putida* (e.g. strains ATCC 12633, DSM 291), *Pseudomonas pyrrocinia* (e.g. strains ATCC 15958, DSM 10685), *Pseudomonas resinovorans* (e.g. strains ATCC 14235, CCUG 2473), *Pseudomonas rhodesiae* (e.g. strains CCUG 38732, DSM 14020), *Pseudomonas saccharophila* (e.g. strains ATCC 15946, DSM 654), *Pseudomonas savastanoi* (e.g. strains ATCC 13522, CFBP 1670), *Pseudomonas spinosa* (e.g. strain ATCC 14606), *Pseudomonas stanieri* (e.g. strains ATCC 27130, DSM 7027), *Pseudomonas straminae* (e.g. strains ATCC 33636, CIP 106745), *Pseudomonas stutzeri* (e.g. strains ATCC 17588, DSM 5190), *Pseudomonas synxantha* (e.g. strains ATCC 9890, CFBP 5591), *Pseudomonas syringae* (e.g. strains ATCC 19310, DSM 6693), *Pseudomonas syzygii* (e.g. strains ATCC 49543, DSM 7385), *Pseudomonas taetrolens* (e.g. strains ATCC 4683, CFBP 5592), *Pseudomonas tolaasii* (e.g. strains ATCC 33618, CCUG 32782), *Pseudomonas veronii* (e.g. strains ATCC 700272, DSM 11331), *Pseudomonas viridiflava* (e.g. strains ATCC 13223, DSM 11124), *Pseudomonas vulgaris*, *Pseudomonas wisconsinensis* and *Pseudomonas spec.* DSM 8246. Among these, preference is given to lipases from *Burkholderia glumae*, *Burkholderia plantarii*, *Burkholderia cepacia*, *Pseudomonas aeruginosa*, *Pseudomonas fluorescens*, *Pseudomonas fragi*, *Pseudomonas luteola*, *Pseudomonas vulgaris*, *Pseudomonas wisconsinensis* and *Pseudomonas spec.* DSM 8246. Particular preference is given to lipases from *Burkholderia specie*, *Burkholderia plantarii* (e.g. strains AZ 8201, ATCC 43733, CCUG 23368, CFBP 3573, CFBP 3997, CIP 105769, DSM 9509, ICMP 9424, JCM 5492, LMG 9035, NCPPB 3590, NIAES 1723).

Examples of *Candida* species are *Candida albomarginata* (e.g. strain DSM 70015), *Candida antarctica* (e.g. strain DSM 70725), *Candida bacarum* (e.g. strain DSM 70854), *Candida bogoriensis* (e.g. strain DSM 70872), *Candida boidinii* (e.g. strains DSM 70026, 70024, 70033, 70034), *Candida bovina* (e.g. strain DSM 70156), *Candida brumptii* (e.g. strain DSM 70040), *Candida cacaoi* (e.g. strain DSM 2226), *Candida cariosilignicola* (e.g. strain DSM 2148), *Candida chalmersii* (e.g. strain DSM 70126), *Candida* ciferii (e.g. strain DSM 70749), *Candida cylindracea* (e.g. strain DSM 2031), *Candida ernobii* (e.g. strain DSM 70858), *Candida famata* (e.g. strain DSM 70590), *Candida freyschussii* (e.g. strain DSM 70047), *Candida friederichii* (e.g. strain DSM 70050), *Candida glabrata* (e.g. strains DSM 6425, 11226, 70614, 70615), *Candida guillermondi* (e.g. strains DSM 11947, 70051, 70052), *Candida haemulonii* (e.g. strain DSM 70624), *Candida inconspicua* (e.g. strain DSM 70631), *Candida ingens* (e.g. strains DSM 70068, 70069), *Candida intermedia* (e.g. strain DSM 70753), *Candida kefyr* (e.g. strains DSM 70073, 70106), *Candida krusei* (e.g. strains DSM 6128, 11956, 70075, 70079, 70086), *Candida lactiscondensi* (e.g. strain DSM 70635), *Candida lambica* (e.g. strains DSM 70090, 70095), *Candida lipolytica* (e.g. strains DSM 1345, 3286, 8218, 70561 or 70562), *Candida lusitaniae* (e.g. strain DSM 70102), *Candida macedoniensis* (e.g. strain DSM 70106), *Candida magnoliae* (e.g. strains DSM 70638, 70639), *Candida membranaefaciens* (e.g. strain DSM 70109), *Candida multigemnis* (e.g. strain DSM 70862), *Candida mycoderma* (e.g. strain DSM 70184), *Candida nemodendra* (e.g. strain DSM 70647), *Candida nitratophila* (e.g. strain DSM 70649), *Candida norvegica* (e.g. strain DSM 70862), *Candida parapsilosis* (e.g. strains DSM 5784, 4237, 11224, 70125, 70126), *Candida pelliculosa* (e.g. strain DSM 70130), *Candida pini* (e.g. strain DSM 70653), *Candida pulcherrima* (e.g. strain DSM 70336), *Candida punicea* (e.g. strain DSM 4657), *Candida pustula* (e.g. strain DSM 70865), *Candida rugosa* (e.g. strain DSM 70761), *Candida sake* (e.g. strain DSM 70763), *Candida silvicola* (e.g. strain DSM 70764), *Candida solani* (e.g. strain DSM 3315), *Candida* sp. (e.g. strain DSM 1247), *Candida spandovensis* (e.g. strain DSM 70866), *Candida succiphila* (e.g. strain DSM 2149), *Candida utilis* (e.g. strains DSM 2361, 70163 or 70167), *Candida valida* (e.g. strains DSM 70169, 70178, 70179), *Candida versatilis* (e.g. strain DSM 6956), *Candida vini* (e.g. strain DSM 70184) and *Candida zeylanoides* (e.g. strain DSM 70185).

Examples of fungal strains of thermophilic *Thermomyces lanuginosus* (GSLMBKU-10, GSLMBKU-13 and GSLMBKU-14).

In the process, according to the presently claimed invention, particular preference is given to using lipases from *Burkholderia plantarii* and *Pseudomonas stutzeri* genera. Preference is given to the immobilized form of this lipase, for example the lipase from *Burkholderia plantarii* immobilized on sodium sulfate.

The amount of hydrolase to be added depends upon its type and the activity of the enzyme preparation. The amount of enzyme optimal for the reaction can be determined easily by simple preliminary experiments. In general, 1000 units of hydrolase/mmol of compound (II) are used.

The reaction of the compound of formula (II) with the acylating agent in step (i) is preferably performed in an organic solvent. Essentially, the organic solvent is selected from the group consisting of ethers selected from the group consisting of diethyl ether, dipropyl ether, diisopropyl ether, dibutyl ether, methyl tertiary butyl ether, ethyl tertiary butyl ether, tetrahydrofuran and dioxane or its mixtures thereof; halogenated hydrocarbons selected from the group consisting of dichloromethane, chloroform, carbon tetrachloride; tetrachloromethane, dichloroethane, tetrachloroethane, chlorobenzene and dichlorobenzene or its mixtures thereof; and aliphatic, cyclic and aromatic hydrocarbon solvent selected from the group consisting of pentane, hexane, cyclopentane, cyclohexane, heptane, octane, cyclooctane, benzene, xylene and toluene or its mixtures thereof.

In an alternatively preferred embodiment, the reaction in step (i) is effected in bulk, i.e. without aqueous or organic solvent.

The step (i) is conducted for a period of $\geq 30$ minutes to $\leq 100$ hours at a temperature in the range of $\geq 0$ to $\leq 70°$ C.; preferably, for a period of $\geq 30$ minutes to $\leq 75$ hours at a temperature in the range of $\geq 10$ to $\leq 60°$ C., more preferably for a period of $\geq 12$ hours to $\leq 24$ hours at a temperature in the range of $\geq 15$ to $\leq 25°$ C.

Essentially, an excess of acylating agent is removed before step (ii) to ensure enantiopurity of the acylated enantiomer. The acylating agent can be removed by any conventional method known in the art including filtration, distillation, extraction, crystallization or chromatography.

For the performance, it is possible, for example, to initially charge the compound of formula (II) with the hydrolase, the acylating agent and, if appropriate, the solvent, and to mix the mixture, for example by stirring or shaking. However, it is also possible to immobilize the hydrolase in a reactor, for example in a column, and to pass a mixture comprising the compound of formula (II) and the acylating agent through the reactor. For this purpose, the mixture can be passed through the reactor in circulation until the desired conversion has been attained. This converts the carboxyl groups of the acylating agent sequentially to hydroxyl of that enantiomer of compound (II) which is acylated enantioselectively, while the other enantiomer remains essentially unchanged. In general, the acylation will be conducted up to a conversion of at least 50%, preferably of at least 75% and, in particular, of at least 90%, based on the enantiomer of compound (II) which is present in the mixture and is acylated enantioselectively. The progress of the reaction, i.e. the sequential acylation, can be monitored by customary methods such as gas chromatography or HPLC (High Performance Liquid Chromatography).

The cineole derivative of formula (II) used is generally the racemate; mixtures in which one of the enantiomers is enriched are, however, also suitable.

The reaction mixture can be worked up in a customary manner, for example by first removing the hydrolase from the reaction mixture, for example by filtering it off or centrifuging it off, if appropriate, removing the solvent from the filtrate or centrifugate, and then subjecting the residue to a separating operation.

The enantioselective conversion of the enantiomer mixture of formula (II) forms a reaction product which comprises essentially an acylated enantiomer of compound (II) and the essentially unacylated opposite enantiomer. This mixture of acylated enantiomer and unacylated enantiomer which is now present can be separated easily by customary methods. Suitable separating operations are, for example, extraction, distillation, crystallization or chromatography. Preference is given to separating the acylated enantiomer and the unacylated enantiomer by extraction.

Essentially, the second enantiomer of the compound of formula (II) in unacylated form is isolated in step (ii) from the mixture containing the first enantiomer of the compounds of formula (II) in acylated form and the second enantiomer of the compounds of formula (II) in unacylated form by subjecting the mixture to the distillation or to the sublimation to a pressure in the range $\geq 1$ to $\leq 500$ Pa and a temperature in the range of $\geq 20$ to $\leq 240°$ C.; preferably, to a pressure in the range $\geq 10$ to $\leq 80$ Pa and at a temperature in the range of $\geq 20$ to $\leq 200°$ C., more preferably to a pressure in the range $\geq 10$ to $\leq 50$ Pa and a temperature in the range of $\geq 20$ to $\leq 100°$ C.

Essentially, the second enantiomer of the compound of formula (II) in unacylated form is isolated in step (ii) from the mixture containing the first enantiomer of the compounds of formula (II) in acylated form and the second enantiomer of the compounds of formula (II) in unacylated form by subjecting the mixture to an extraction in which the pH of the aqueous phase is adjusted to pH ≥7 and <9 by addition of a base. The first enantiomer in acylated form is extracted into the aqueous phase leaving second enantiomer in unacylated form in the organic phase.

Essentially, the base used in the extraction is a weak base or a strong base.

Essentially, the base is selected from sodium carbonate, sodium bicarbonate, ammonium hydroxide, sodium hydroxide, and potassium hydroxide.

Preferably, the base is a weak base.

Essentially, the second enantiomer of the compound of formula (II) in unacylated form is isolated in step (ii) from the mixture containing the first enantiomer of the compounds of formula (II) in acylated form and the second enantiomer of the compounds of formula (II) in unacylated form by subjecting the mixture to the extraction three times with an aqueous solution of the weak base at pH <9 followed by combining the extracts. The pH of the combined aqueous extracts is adjusted to ≥9 to isolate the second enantiomer of the compound of formula (II) in unacylated form.

Essentially, the weak base is selected from sodium carbonate, sodium bicarbonate and ammonium hydroxide. Preferably, the weak base is sodium bicarbonate.

Preferably, the base is an aqueous solution of weak base. More preferably, the base is aqueous solution of sodium bicarbonate.

Essentially, in the extraction the second enantiomer of the compound of formula (II) in unacylated form is extracted in organic phase leaving the first enantiomer of the compound of formula (II) in acylated form in the aqueous phase.

The basic conditions need to perform saponification in step (iii) are obtained by using an inorganic base in a polar solvent.

In another embodiment of the presently claimed invention, the polar solvent is selected from the group consisting of alcohol and water. Preferably the alcohols are selected from the group consisting of methanol, ethanol, n-propanol, n-butanol, iso-butanol, and amyl alcohol.

The polar solvent used in step (iii) is selected from the group consisting of alcohol selected from the group consisting of methanol, ethanol, n-propanol, n-butanol, iso-butanol, amyl alcohol; and water; or its mixtures thereof.

The process of the claimed invention further increases the enantiomeric excess of the optically active compound of formula (II-R) or the optically active compound of formula (II-S) by lixiviation and crystallization in which the enantiomer of formula (II-R) or (II-S) is suspended in at least one non-polar solvent in step (v) followed by stirring the suspension obtained in step (v) at a temperature in the range of ≥10° C. to reflux temperature of the non-polar solvent; and in step (vii) enantiomerically enriched crystals of optically active compound of formula (II-R) or formula (II-S) are isolated.

The process of the claimed invention further increases the enantiomeric excess of the optically active compound of formula (IIa-R) or the optically active compound of formula (IIa-S) by lixiviation and crystallization in which the enantiomer of formula (IIa-R) or (IIa-S) is suspended in at least one non-polar solvent in step (v) followed by stirring the suspension obtained in step (v) at a temperature in the range of ≥10° C. to reflux temperature of the non-polar solvent; and in step (vii) enantiomerically enriched crystals of optically active compound of formula (IIa-R) or formula (IIa-S) are isolated.

The process of the claimed invention further increases the enantiomeric excess of the optically active compound of formula (IIa-R) or the optically active compound of formula (IIa-S) by adding seed crystals of the desired enantiomer of formula (II-R) or formula (II-S) in step (vi).

Essentially, in step (v) the suspension is stirred at a temperature in the range of ≥10 to ≤120° C., preferably ≥20 to ≤115° C.

Essentially, in step (vii) the isolation of the crystals of the desired enantiomer is carried out at temperature in the range of ≥−10 to ≤30° C., preferably ≥10 to ≤25° C.

Essentially, in step (vii) the desired enantiomer is isolated by a method selected from the group consisting of filtration or evaporation.

Essentially, in step (v) the non-polar solvent is a solvent having polarity index ≥0.0 to ≤4.0. Preferably, the non-polar solvent is a hydrocarbon. More preferably, the non-polar solvent is a hydrocarbon having polarity index of ≥0.0 to ≤2.5.

Essentially, in step (v), the non-polar solvent used is a hydrocarbon selected from the group consisting of pentane, hexane, cyclopentane, cyclohexane, heptane, octane, cyclooctane, benzene, xylene and toluene or its mixtures thereof.

The process according to the presently claimed invention affords the optically active oxabicyclo[2.2.1]heptan-2-yl derivative of formula (IIa-S) and formula (IIa-R) with an enantiomeric excess (ee) of preferably at least 70% ee, more preferably of at least 80% ee, even more preferably of at least 90% ee and in particular of at least 99% ee, for example at least 99.5% ee.

Preferably, the optically active oxabicyclo[2.2.1]heptan-2-yl derivative of formula (IIa-R) is [(1S,2R,4R)-4-isopropyl-1-methyl-7-oxabicyclo[2.2.1]heptan-2-yl] dodecanoate with an enantiomeric excess (ee) of preferably at least 70% ee, more preferably of at least 80% ee, even more preferably of at least 90% ee and in particular of at least 99% ee, for example at least 99.5% ee.

Preferably, the optically active oxabicyclo[2.2.1]heptan-2-yl derivative of formula (IIa-S) is [(1R,2S,4S)-4-isopropyl-1-methyl-7-oxabicyclo[2.2.1]heptan-2-yl] dodecanoate with an enantiomeric excess (ee) of preferably at least 70% ee, more preferably of at least 80% ee, even more preferably of at least 90% ee and in particular of at least 99% ee, for example at least 99.5% ee.

Preferably, the optically active oxabicyclo[2.2.1]heptan-2-yl derivative of formula (IIa-R) is 4-[[(1R,2S,4S)-4-isopropyl-1-methyl-7-oxabicyclo[2.2.1]heptan-2-yl]oxy]-4-oxo-butanoic acid with an enantiomeric excess (ee) of preferably at least 70% ee, more preferably of at least 80% ee, even more preferably of at least 90% ee and in particular of at least 99% ee, for example at least 99.5% ee.

Preferably, the optically active compound of formula (IIa-S) is 4-[[(1S,2R,4R)-4-isopropyl-1-methyl-7-oxabicyclo[2.2.1]heptan-2-yl]oxy]-4-oxo-butanoic acid with an enantiomeric excess (ee) of preferably at least 70% ee, more preferably of at least 80% ee, even more preferably of at least 90% ee and in particular of at least 99% ee, for example at least 99.5% ee.

The enantiomerically enriched optically active cineole derivative of formula (II-R) or formula (II-S) obtained according to the process of the presently claimed invention is used for preparing an optically active oxabicyclo[2.2.1]heptan-2-yl derivative of formula (I-R) or (1-5).

Finally, the invention provides a process for preparing an optically active oxabicyclo[2.2.1]heptan-2-yl derivative of formula (I-R) or (1-S) in which the optically active cineole derivative of formula (II-R) or formula (II-S) obtained according to the process of the presently claimed invention is treated with a compound of formula (III)

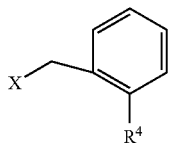

formula (III)

wherein X is a leaving group and $R^4$ is unsubstituted or substituted alkyl, in the presence of a non-polar solvent and in the presence of a base.

Essentially, the leaving group X is selected from the group consisting of halogen, an oxygen linked leaving group, an ammonium group of formula (IV);

$$-N(R'_1)(R'_2)(R'_3)^+Y^- \qquad (IV)$$

wherein $R'_1$, $R'_2$ and $R'_3$ are each independently selected from $C_1$-$C_6$-alkyl, $C_3$-$C_{10}$-cycloalkyl and $C_6$-$C_{20}$-aryl, and $Y^-$ is selected from halide, hydroxide, $C_1$-$C_4$-alkyl sulfonate and $C_6$-$C_{20}$-aryl sulfonate ions.

Preferably, halogen is selected from a chlorine, a bromine, an iodine and a fluorine.

Preferably, oxygen linked leaving groups are selected from group consisting of $C_1$-$C_4$-alkyl sulfonates, $C_1$-$C_4$-haloalkyl sulfonates, $C_6$-$C_{20}$-aryl sulfonates, $C_3$-$C_{10}$-cycloalkyl sulfonates and imidazolylsulfonate (imidazylate), more preferably from $C_1$-$C_4$-alkyl sulfonates, $C_1$-$C_4$-haloalkyl sulfonates and $C_6$-$C_{20}$-aryl sulfonates and even more preferably from $C_1$-$C_4$-alkyl sulfonates and $C_6$-$C_{20}$-aryl sulfonates.

Examples of $C_1$-$C_4$-alkyl sulfonates include but are not limited to mesylate (methanesulfonate), esylate (ethanesulfonate), n-propylsulfonate, iso-propylsulfonate, n-butylsulfonate, iso-butylsulfonate, sec-butylsulfonate and tert-butylsulfonate.

Examples of $C_1$-$C_4$-haloalkyl sulfonates include but are not limited to triflate (trifluoromethanesulfonate) and trichloromethanesulfonate.

Examples of $C_3$-$C_{10}$-cycloalkyl sulfonates include but are not limited to cyclohexylsulfonate.

Examples of $C_6$-$C_{20}$-aryl sulfonates include but are not limited to tosylate (p-toluenesulfonate), besylate (benzenesulfonate) and 2-naphtyl sulfonate.

Preferably, the oxygen linked leaving group is selected from mesylate (methanesulfonate), esylate (ethanesulfonate), n-propylsulfonate, iso-propylsulfonate, n-butylsulfonate, iso-butylsulfonate, sec-butylsulfonate, tert-butylsulfonate, triflate (trifluoromethanesulfonate), trichloromethanesulfonate, tosylate (p-toluenesulfonate), besylate (benzenesulfonate), 2-naphtyl sulfonate, cyclohexylsulfonate and imidazolylsulfonate (imidazylate), more preferably from mesylate, esylate, triflate, tosylate and besylate and even more preferably from mesylate and tosylate.

Preferably, ammonium group of formula (IV)

$$-N(R'_1)(R'_2)(R'_3)^+Y^- \qquad (IV)$$

wherein $R'_1$, $R'_2$ and $R'_3$ are each independently selected from $C_1$-$C_6$-alkyl and $Y^-$ is selected from halide, hydroxide, $C_1$-$C_4$-alkyl sulfonate and $C_6$-$C_{20}$-aryl sulfonate ions.

Preferably, ammonium group of formula (IV) wherein $R'_1$, $R'_2$, and $R'_3$ are each independently selected from $C_1$-$C_6$-alkyl and $Y^-$ is selected from a chlorine, bromine, iodine, hydroxide, mesylate and tosylate ion.

Examples of ammonium group of formula (IV) include but are not limited to a trimethyl ammonium chloride group of formula (IVa);

$$-N(CH_3)_3^+Cl^- \qquad (IVa),$$

and a triethyl ammonium chloride group of formula (IVb)

$$-N(CH_2CH_3)_3^+Cl^- \qquad (IVb).$$

In another embodiment of the presently claimed invention, the leaving group X is preferably bromine.

Preferably, the compound of formula (III) is o-methyl benzyl bromide.

Essentially, the non-polar solvent used in said process is a hydrocarbon selected from the group consisting of pentane, hexane, cyclopentane, cyclohexane, heptane, octane, cyclooctane, benzene, xylene and toluene or its mixtures thereof.

The process according to the presently claimed invention affords the optically active oxabicyclo[2.2.1]heptane derivative of formula (I-S) and formula (I-R) with an enantiomeric excess (ee) of preferably at least 90% ee, more preferably of at least 95% ee, even more preferably of at least 99% ee and in particular of at least 99.5% ee, for example at least 99.9% ee.

Preferably, the optically active oxabicyclo[2.2.1]heptane derivative of formula (I) compound is (1S,2R,4R)-4-isopropyl-1-methyl-2-(o-tolylmethoxy)-7-oxabicyclo[2.2.1]heptane with an enantiomeric excess (ee) of preferably at least 96% ee, more preferably of at least 97% ee, even more preferably of at least 98% ee and in particular of at least 99% ee, for example at least 99.9% ee.

Preferably, the optically active oxabicyclo[2.2.1]heptane derivative of formula (I) compound is (1R,2S,4S)-4-isopropyl-1-methyl-2-(o-tolylmethoxy)-7-oxabicyclo[2.2.1]heptane with an enantiomeric excess (ee) of preferably at least 96% ee, more preferably of at least 97% ee, even more preferably of at least 98% ee and in particular of at least 99% ee, for example at least 99.9% ee.

The enantiomeric excess of the compound of formulae (II-S), (II-R), (IIa-R), (IIa-S), (1-R) and (1-S) can be determined by means of common processes, for example by determining the optical rotation or by chromatography on a chiral phase, for example by HPLC or gas chromatography using chiral columns.

When there is no interest in one of the enantiomers or in reaction products thereof, it can be racemized and reused in step (i). This recycling makes it possible to obtain more than 50% of the desired enantiomer (S) or (R) overall from the enantiomer mixture (II).

The reaction product can be further purified by customary processes, for example by distillation, sublimation, extraction or chromatography.

The remarks made above regarding suitable and preferred embodiments of the invention and of the process apply here correspondingly.

The process according to the presently claimed invention affords the desired enantiomer of cineole derivative or oxabicyclo[2.2.1]heptane derivative in high yields and with a very high enantiomeric purity.

The present invention is illustrated by the non-restrictive examples which follow.

EXAMPLES

Chemicals Used:
1. Racemic 2-hydroxy-1,4-cineole;
2. 2-hydroxy-1,4-cineole (enantiomeric ratio R:S=40:60);
3. Methyl tert-butyl ether (MTBE);
4. Silica;
5. Enzymes: Lipase BP.; Novozyme 435; Lipase PS-D Amano I; *Candida antarctica* lipase A; Amano Lipase PS-D; Lipase from *Candida lipolytica*; Lipase from *Mucor javanicus*; Lipase from *Rhizopus niveus*; Amano Lipase M from *Mucor javanicus*; Amano Lipase F-AP15 *Rhizopus oryzae*; Lipase AS Amano LAY06514555 Japan; Lipozyme TL IM LA 331067 *Thermomyces lanugenosus*; Lipase A Amano 12 LJ 1050608 Japan; Amano Lipase AK from *Pseudomonas fluorescens*; Lipase PS from *Pseudomonas stutzeri*; and Lipase from *Candida parapsi-lopsis;*
6. Succinic anhydride;
7. NaHCO$_3$;
8. NaOH;
9. Na$_2$SO$_4$
10. Vinyl Dodecanoate;
11. CsCl;
12. n-heptane;
13. Toluene;
14. Methanol;
15. Brine;
16. Water;
17. Diethyl ether;
18. Cyclohexane;
19. Ethyl acetate; and
20. o-methyl-benzylbromide.

Analytical Methods Used:
A. Optical purity determined by Chiral GC (Standard method using a chiral GC-column like Hydrodex-β-6 TBDM, Macherey & Nagel, 25 m×0.25 mm×0.25 μm);
B. Conversion determined by achiral GC (Standard Method using a GC-column like Chrompack CP Sil-8-CB, Agilent J&W, 30 m×0.32 mm×1 μm);
C. Optical rotation determined by Polarimeter (Jasco P-1010); and
D. $^1$H-NMR determined by Bruker Avance 400.

Enzyme Screening:

A screen of 16 commercially available enzymes was undertaken to identify enzymes showing high pro S- or R-selectivity for the O-acylation of hydroxy cineol using vinyl dodecanoate in MTBE.

1.0 g (5.8 mmol) of racemic hydroxycineol was dissolved in MTBE (20 mL). To this, 0.65 g (3.1 mmol) of vinyl dodecanoate was added, followed by the addition of 200 mg of each enzyme catalyst. The mixture was shaken with 150 rpm in a stoppered flask and the reaction mixture was analyzed by chiral GC for enantiomeric excess and by achiral GC for conversion. The results are tabulated below:

TABLE 1

Results of Enzyme Screening

| Sr. No. | Enzyme | Time in Hours | ee of unreacted enantiomer R-3 [%] | Conversion in % | Selectivity [E] |
|---|---|---|---|---|---|
| 1 | Lip. BP 50% on Na$_2$SO$_4$ | 3 | 19 | 14.5 | |
| | | 20 | 62 | 41.5 | 40 |
| 2 | Novozyme 435 | 3 | 2 | 0.2 | |
| | | 18 | 5 | 1 | |
| 3 | Lipase PS-D Amano I | 20 | 7 | 5 | |
| | | 41 | 30 | 13 | ≥500 |
| 4 | *Candida antarctica* lipase A | 20 | 2 | 15 | 1 |
| | | 117 | 9 | 50 | 1 |
| 5 | Amano Lipase PS-D | 24 | 7 | 3 | |
| | | 48 | 15 | 7.5 | ≥500 |
| 6 | Lipase from *Candida lipolytica* | 24 | 0 | 0 | |
| | | 93 | 0 | 0 | |
| 7 | Lipase from *Mucor javanicus* | 24 | 0 | 0 | |
| | | 93 | 0 | 0 | |
| 8 | Lipase from *Rhizopus niveus* | 24 | 0 | 0 | |
| | | 93 | 0 | 0 | |
| 9 | Amano Lipase M from *Mucor javanicus* | 24 | 0 | 0 | |
| | | 48 | 1 | 0 | |
| 10 | Amano Lipase F-AP15 *Rhizopus oryzae* | 24 | 2 | 0 | |
| | | 48 | 2 | 0 | |
| 11 | Lipase AS Amano LAY06514555 Japan | 24 | 0 | 0 | |
| | | 48 | 0 | 0 | |
| 12 | Lipozyme TL IM LA 331067 *Thermomyces lanugenosus* | 24 | 13 | 13 | 15 |
| | | 48 | 28 | 30 | 10 |
| 13 | Lipase A Amano 12 LJ 1050608 Japan | 24 | 0 | 0 | |
| | | 48 | 0 | 0 | |
| 14 | Amano Lipase AK from *Pseudomonas fluorescens* | 24 | 0 | 0.1 | |
| | | 48 | 0 | 0.7 | |
| 15 | Lipase PS from *Pseudomonas stutzeri* | 24 | 41 | 28.5 | 140 |
| | | 48 | 41 | 28.6 | 140 |
| 16 | Lipase from *Candida parapsi-lopsis* | 24 | 0 | 0.8 | |
| | | 48 | 0 | 2.0 | |

Out of 16 lipases tested, the lipase BP from *Burkholderia plantarii* was the most active one with satisfactory selectivity (E=40). An even higher selectivity (E=140) was achieved in the case of lipase from *Pseudomonas stutzerii* (supplier: Amano). Unfortunately, the reaction with this catalyst proceeded relatively slowly, therefore experiments on a preparative scale were done using BPLipase as the catalyst Example 1

Resolution of 2-Hydroxy-1,4-Cineole with Succinic Anhydride as the Acylation Agent 176 g (1,029 mol) 2-hydroxy-1,4-cineole (enantiomeric ratio R:S=40:60) were dissolved in MTBE (2570 mL). 102.9 g (1.029 mol) of finely ground succinic anhydride and 4.4 g (2.5 wt-%) of lipase from *Burkholderia plantarii* immobilized on Na$_2$SO$_4$ (carrier loaded with 50% protein) were added. The mixture was stirred for 24 hours, then non-dissolved material was removed by filtration over a short path of silica.

A. Isolation of the S-Enantiomer:

400 mL of 10% NaHCO$_3$ were added to the clear filtrate and the biphasic mixture was stirred vigorously for 30 minutes. After standing for another 30 minutes the aqueous phase was removed. Extraction with NaHCO$_3$ was repeated two times and the organic phase was finally washed with water (100 mL). The organic phase comprising the R-isomer was separated from the aqueous phase.

The pH of the combined aqueous phases was adjusted to >12 by the addition of 50% NaOH (50 mL) and stirred for 7 hour at 70° C. The mixture was cooled to room temperature and extracted twice with 200 mL each of MTBE. The combined organic extracts were dried over $Na_2SO_4$, filtrated through a short path of silica and concentrated. The remainder obtained was 30.5 g (17%) of S-hydroxycineol as white crystals. The enantiomeric ratio (R:S) was determined to be 15% R: 85% S.

B. Isolation of the R-Enantiomer:

The organic phase containing the R-isomer separated from the $NaHCO_3$ extraction of step (A) was dried over $Na_2SO_4$ and concentrated to give 145 g (82%) of R-Hydroxycineol as slightly greyish crystals. The enantiomeric ratio (R:S) was determined to be 88% R: 12% S.

Example 2

Resolution of 2-Hydroxy-1,4-Cineole with Vinyl Dodecanoate as the Acylation Agent, Targeting Pure R-Enantiomer A. Isolation of Pure R-Enantiomer:

20.4 g (0.12 mol) of racemic 2-hydroxy-1,4-cineole was dissolved in MTBE (200 mL). To this, 26.6 g (0.12 mol) of vinyl dodecanoate was added, followed by the addition of 500 mg of *Burkholderia plantarii* lipase (50% immobilized on $Na_2SO_4$). The mixture was stirred at room temperature for 70 hours. The enzyme catalyst was removed from the mixture by filtration. The clear filtrate so obtained was concentrated in vacuum and the remainder was subjected to sublimation (0.1 mbar, 55° C.). As a sublimate 5 g of 83:17 mixture of R-hydroxycineol and vinyl dodecanoate were obtained. This was stirred at room temperature with n-heptane (20 mL) for 4 hours. The precipitated solid material was isolated by filtration and dried in vacuum. 3.5 g (17%) of R-hydroxycineol were obtained, the material was enantiopure. The optical purity was >99.9% ee.

B. Isolation of Enantioenriched S-Enantiomer:

The non-volatile remainder from the sublimation of step (A) was dissolved in methanol (15 mL) and 25% NaOH (40 g) was added. The resulting mixture was stirred at 60° C. for 6 hours, then the methanol was removed in vacuum. The remainder was diluted with water (50 mL) and extracted twice with MTBE (100 mL each). The combined extracts were washed with water (10 mL) and dried over $Na_2SO_4$. After removal of the solvent, 12.5 g (61%) of S-Hydroxycineol were obtained as colorless crystals, the optical purity was 57% ee.

Example 3

Resolution of 2-Hydroxy-1,4-Cineole with Vinyl Dodecanoate as the Acylation Agent, Targeting Pure S-Enantiomer A. Isolation of Enantioenriched R-Enantiomer:

20.4 g (0.12 mol) of racemic 2-hydroxy-1,4-cineole was dissolved in MTBE (200 mL). To this, 13.3 g (0.06 mol) of vinyl dodecanoate was added, followed by the addition of 500 mg of *Burkholderia plantarii* lipase (50% immobilized on $Na_2SO_4$). The mixture was stirred at room temperature for 70 hours, then the enzyme catalyst was removed by filtration. The clear filtrate was concentrated in vacuum and the remainder was subjected to sublimation (0.1 mbar, 55° C.). As a sublimate 9 g (44%) of R-hydroxycineol were obtained, the optical purity was 71% ee.

B. Isolation of Pure S-Enantiomer:

The non-volatile remainder (17 g) from the sublimation of step (A) was dissolved in methanol (15 mL) and 25% NaOH (40 g) was added. The resulting mixture was stirred at 60° C. for 6 hours, then the methanol was removed in vacuum. The remainder was diluted with water (50 mL) and extracted twice with MTBE (100 mL each). The combined extracts were washed with water (10 mL) and dried over $Na_2SO_4$. After removal of the solvent, 4.9 g (24%) of S-hydroxycineol were obtained as colorless crystals, the optical purity was 87% ee.

Example 4

Isolation of Enantiopure (R)-2-Hydroxy-1,4-Cineole by Lixiviation 3.8 g of enantioenriched R-hydroxycineol (ee: 50%; R:S=75:25) obtained according to Example 1 was stirred at room temperature with n-heptane (22 mL) for 8 hours. Insoluble material was filtrated, washed with cold n-heptane (3 mL) and dried. 1.85 g of 99% ee (R:S=99.5:0.5) hydroxycineol was obtained as a white powder, m.p.: 89° C.

The filtrates were combined and evacuated to dryness. 1.95 g of almost racemic hydroxyl-cineol (ee=4%; R:S=52:48) were obtained as a white powder, m.p.: 56° C.

The racemate so obtained was recycled in Example-1.

Example 5

Isolation of Enantiopure (S)-2-Hydroxy-1,4-Cineole by Crystallization 30.5 g of crude S-hydroxy-cineol (ee: 70%, R:S=15:85) obtained according to Example 1 was suspended in n-heptane (125 mL) and stirred at reflux temperature of n-heptane. A clear solution was obtained. Upon cooling to room temperature, purified material precipitated as white crystals. The precipitate was filtered of, washed with cold n-heptane (10 mL) and dried, yielding 17.9 g (57%) of pure S-enantiomer (ee: >99%), m.p.: 86° C.

By concentrating the mother liquors, 9 g (30%) of nearly racemic (R:S=45:55) hydroxy-cineol was obtained as a white solid, m.p.: 55° C.

The racemate so obtained was recycled in Example-1.

Example 6

Preparation of enantiopure [(1R,2S,4S)-4-isopropyl-1-methyl-7-oxabicyclo[2.2.1]heptan-2-yl] dodecanoate 2 g (11.8 mmol) of S-hydroxy cineol (ee: >99%) obtained according to Example 5 was dissolved in MTBE (50 mL). To this, 2.92 g (13 mmol) of vinyl dodecanoate was added, followed by the addition of 200 mg of *Burkholderia plantarii* lipase (50% immobilized on $Na_2SO_4$). The mixture was shaken (150 rpm) at room temperature for 72 hours, then the enzyme catalyst was removed by filtration. The solvent was removed in vacuum (20 mbar) and the remaining colorless oil was further concentrated in high vacuum (0.1 mbar, 155° C.). After 4 hours at these conditions the remainder was analyzed by GC, showing that the product, [(1R,2S,4S)-4-isopropyl-1-methyl-7-oxabicyclo[2.2.1]heptan-2-yl] dodecanoate, was 99.6% pure. Yield: 3.9 g (94%) of a colorless, highly viscous oil.

$^1$H-NMR (400 MHz, $CDCl_3$):

δ=0.88 (t, J=7 Hz, 3H), 0.92 (d, J=7 Hz, 3H), 0.97 (d, J=7 Hz, 3H), 1.20-1.38 (m, 16H), 1.40 (s, 3H), 1.43-1.58 (m, 2H), 1.63 ($m_c$, 5H), 2.05-2.22 (m, 2H), 2.30 ($m_c$, 2H), 4.88 (dd, J=10 und 4 Hz, 1H).

Optical Rotation:

[α]$_D$=+22° (c=2 in EtOH)

Example 7

Preparation of enantiopure 4-[[(1R,2S,4S)-4-isopropyl-1-methyl-7-oxabicyclo[2.2.1]heptan-2-yl]oxy]-4-oxo-butanoic Acid 2 g (11.8 mmol) of S-hydroxy cineol (ee: >99%) obtained according to Example 5 was dissolved in MTBE (50 mL). To this, 1.29 g (13 mmol) of finely ground succinic anhydride was added followed by the addition of 200 mg of *Burkholderia plantarii* lipase (50% immobilized on $Na_2SO_4$). The mixture was shaken (150 rpm) at room temperature for 72 hours, then the enzyme catalyst was removed by filtration. The clear filtrate was extracted three times with 20 mL each of 10% $NaHCO_3$ solution. The combined extracts were shortly evaporated to remove residual solvents, then the solution was cooled to 5° C. and the pH was adjusted to 2.5 by the addition of 10% HCl. The mixture was extracted twice with 30 mL each of diethyl ether and the combined extracts were dried over $Na_2SO_4$. Evaporation of the solvent left a colorless, highly viscous oil which was further dried in vacuum (0.1 mbar, 120° C.) until a GC-sample showed that the product, 4-[[(1R,2S,4S)-4-isopropyl-1-methyl-7-oxabicyclo[2.2.1]heptan-2-yl]oxy]-4-oxo-butanoic acid, was >99% pure. Yield: 2.8 g (80%) of a colorless, highly viscous oil.

$^1$H-NMR (400 MHz, $CDCl_3$):

δ=0.95 (d, J=7 Hz, 3H), 1.00 (d, J=7 Hz, 3H), 1.36-1.42 (m, 1H), 1.38 (s, 3H), 1.50-1.70 (m, 4H), 2.05-2.22 (m, 2H), 2.60-2.76 (m, 4H), 4.90 (dd, J=10 und 4 Hz, 1H), 10.15 (s broad, 1H).

Optical Rotation:

[α]$_D$=+31.5° (c=2 in EtOH)

Example 8

Preparation of enantiopure Cinmethylin (1R,2S,4S)-Enantiomer [(1R,2S,4S)-4-isopropyl-1-methyl-2-(o-tolylmethoxy)-7-oxabicyclo[2.2.1]heptane.]

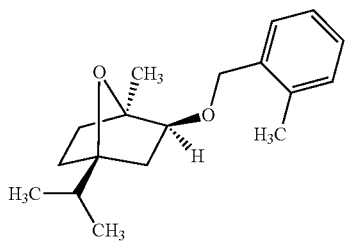 [SMILES: Cc1ccccc1CO[C@H]1CC[C@]2(C(C)C)CC[C@@]1(C)O2]

10 g (59 mmol) S-hydroxycineol (enantiomeric purity=99.9% ee) obtained according to example 4 or 5 was dissolved in toluene (100 mL). Powdered NaOH (3.05 g, 76 mmol) and 0.2 g (1.2 mmol) CsCl was added and the mixture was heated on a Dean-Stark-Trap for 6 hours. Then 10.9 g (60 mmol) of o-methyl-benzylbromide was added dropwise and heating was continued for another 60 hours.

Water (100 mL) was added to the cooled reaction mixture and the phases were separated. The organic layer was extracted twice with brine (20 mL each) and dried over $Na_2SO_4$. The solvent is removed in vacuum to obtain a yellowish oil. The volatile material from the oil was removed in vacuum (bath: 75° C., pressure: 0.1 mbar). The remainder was subjected to column chromatography (eluent: cyclohexane/ethyl acetate 98:2 v/v) yielding a 99.2% pure cinmethylin which was further purified by bulb-to-bulb distillation (0.1 mbar, 135° C.). Finally 8.5 g (53%) of 1R,2S,4S-cinmethylin with a chemical purity of 99.9% was obtained as a colorless oil.

Optical rotation: [α]D: +58.2° (pure, d=0.99 g/cm$^3$) [α]D: +67.4° (c=5 in ethanol)

Example 9

Preparation of enantiopure Cinmethylin (1S,2R,4R)-Enantiomer [(1S,2R,4R)-4-isopropyl-1-methyl-2-(o-tolyl methoxy)-7-oxabicyclo[2.2.1]heptane]

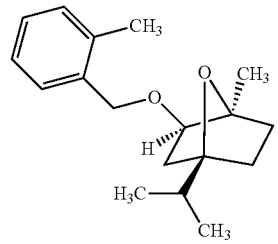 [SMILES: Cc1ccccc1CO[C@@H]1C[C@@]2(C(C)C)CCC[C@]1(C)O2]

Following the procedure according to example 6, starting from 10 g (59 mmol) R-hydroxycineol (enantiomeric purity=99.9% ee) obtained according to example 4 or 5 yielded 7.5 g (46%) of 1S,2R,4R-cinmethylin with a chemical purity of 99.96%.

Optical Rotation:

[α]D: −57.9° (pure, d=0.99 g/cm$^3$) [α]D: −68.5° (c=5 in ethanol)

The invention claimed is:

1. A process for preparing an optically active compound of formula (II-R),

formula (II-R)

or an optically active compound of formula (II-S),

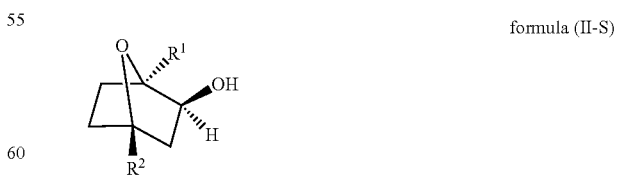

formula (II-S)

wherein $R^1$ is selected from the group consisting of hydrogen and unsubstituted or substituted alkyl and $R^2$ is selected from the group consisting of hydrogen and unsubstituted or substituted alkyl;

said process comprises at least the steps of:
(i) reacting a first mixture comprising a compound of formula (II)

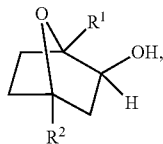
(II)

with an acylating agent in the presence of a hydrolase to obtain a second mixture containing a first enantiomer of the compounds of formula (II) in acylated form and a second enantiomer of the compounds of formula (II) in unacylated form, wherein:
$R^1$ and $R^2$ in formula (II) are as defined above, and
the hydrolase is selected from the group consisting of lipases from bacteria of the *Burkholderia* genera, lipases from bacteria of the *Pseudomonas* genera, and lipases from fungal strains of *Thermomyces*; and
(ii) isolating the second enantiomer of the compound of formula (II) in unacylated form from the second mixture of step (i) to obtain an optically active compound of formula (II-R) or an optically active compound of formula (II-S) and a third mixture containing the first enantiomer of the compounds of formula (II) in acylated form.

2. The process of claim 1, further comprising the steps of
(iii) subjecting the third mixture of step (ii) to basic saponification to obtain a fourth mixture containing the first enantiomer of the compounds of formula (I) in unacylated form; and
(iv) isolating the first enantiomer of the compounds of formula (I) in unacylated form from the fourth mixture of step (iii) to obtain an optically active compound of formula (II-R) or an optically active compound of formula (II-S).

3. The process of claim 2, further comprising the steps of
(v) providing a suspension comprising the optically active compound of formula (II-R) or formula (II-S) as obtained in step (iv) in at least one non-polar solvent;
(vi) stirring the suspension obtained in step (v) at temperature in the range of ≥10° C. to reflux temperature of the non-polar solvent; and
(vii) isolating crystals of the optically active enantiomer of formula (II-R) or formula (II-S) obtained in step (vi).

4. The process of claim 3, further comprising adding seed crystals of a desired enantiomer of formula (I-R) or formula (I-S) in step (vi).

5. The process of claim 1, wherein in the second mixture in step (i), the first enantiomer of the compounds of formula (II) in acylated form is the optically active compound of formula (II-S) and the second enantiomer of the compounds of formula (II) in unacylated form is the optically active compound of formula (II-R).

6. The process of claim 1, wherein the acylating agent is selected from the group consisting of a vinyl or propenyl ester of a saturated aliphatic carboxylic acid; aliphatic alkyl ester of a saturated cycloaliphatic carboxylic acid; and saturated aliphatic carboxylic acid anhydride.

7. The process of claim 1, wherein in step (i) the compound of formula (II) and the acylating agent is reacted for a period of ≥30 minutes to ≤100 hours at a temperature in the range of ≥0 to ≤70° C.

8. The process of claim 1, wherein an excess of acylating agent is removed before step (ii).

9. The process of claim 1, wherein in step (ii) the second enantiomer of the compound of formula (II) in unacylated form is isolated from the second mixture containing the first enantiomer of the compounds of formula (II) in acylated form and the second enantiomer of the compounds of formula (II) in unacylated form by subjecting the second mixture to a pressure in the range ≥10 to ≤500 Pa and a temperature in the range of ≥20 to ≤240° C.

10. A process for preparing an optically active compound of formula (I-R),

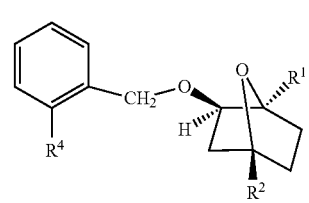
formula (I-R)

or optically active compounds of formula (I-S),

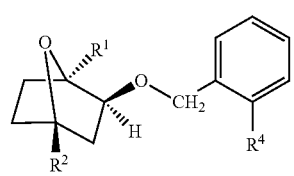
formula (I-S)

wherein
$R^1$ is selected from hydrogen and unsubstituted or substituted alkyl;
$R^2$ is selected from hydrogen and unsubstituted or substituted alkyl; and
$R^4$ is unsubstituted or substituted alkyl;
the method comprising:
preparing an optically active compound of formula (II-R),

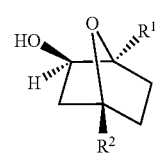
formula (II-R)

or an optically active compound of formula (II-S),

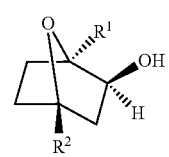
formula (II-S)

wherein
R¹ is selected from the group consisting of hydrogen and unsubstituted or substituted alkyl and
R² is selected from the group consisting of hydrogen and unsubstituted or substituted alkyl;
said process comprises at least the steps of:
(i) reacting a first mixture comprising a compound of formula (II)

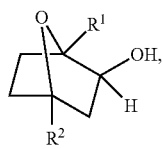
(II)

with an acylating agent in the presence of a hydrolase to obtain a second mixture containing a first enantiomer of the compounds of formula (II) in acylated form and a second enantiomer of the compounds of formula (II) in unacylated form, wherein:
R¹ and R² in formula (II) are as defined above, and
the hydrolase is selected from the group consisting of lipases from bacteria of the *Burkholderia* genera, lipases from bacteria of the *Pseudomonas* genera, and lipases from fungal strains of *Thermomyces*;
(ii) isolating the second enantiomer of the compound of formula (II) in unacylated form from the second mixture of step (i) to obtain an optically active compound of formula (II-R) or an optically active compound of formula (II-S) and a third mixture containing the first enantiomer of the compounds of formula (II) in acylated form; and
(iii) reacting the optically active compound of formula (II-R) or the optically active compound of formula (II-S) in the presence of a non-polar solvent and in the presence of a base with a compound of formula (III)

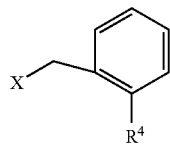
formula (III)

wherein X is a leaving group and R⁴ is unsubstituted or substituted alkyl.

11. The process according to claim 10, wherein the optically active compound of formula (I-R) and (I-S) is selected from the group consisting of (1R,2S,4S)-4-isopropyl-1-methyl-2-(o-tolylmethoxy)-7-oxabicyclo[2.2.1]heptane and (1S,2R,4R)-4-isopropyl-1-methyl-2-(o-tolylmethoxy)-7-oxabicyclo[2.2.1]heptane.

12. The process of claim 2, wherein the acylating agent is selected from the group consisting of a vinyl or propenyl ester of a saturated aliphatic carboxylic acid; aliphatic alkyl ester of a saturated cycloaliphatic carboxylic acid; and saturated aliphatic carboxylic acid anhydride.

13. The process of claim 3, wherein the acylating agent is selected from the group consisting of a vinyl or propenyl ester of a saturated aliphatic carboxylic acid; aliphatic alkyl ester of a saturated cycloaliphatic carboxylic acid; and saturated aliphatic carboxylic acid anhydride.

14. The process of claim 4, wherein the acylating agent is selected from the group consisting of a vinyl or propenyl ester of a saturated aliphatic carboxylic acid; aliphatic alkyl ester of a saturated cycloaliphatic carboxylic acid; and saturated aliphatic carboxylic acid anhydride.

15. The process of claim 1, wherein in the second mixture in step (i), the first enantiomer of the compounds of formula (II) in acylated form is the optically active compound of formula (II-R) and the second enantiomer of the compounds of formula (II) in unacylated form is the optically active compound of formula (II-S).

16. The process of claim 1, wherein the hydrolase is selected from the group consisting of lipases from bacteria of the *Burkholderia* genera.

17. The process of claim 16, wherein the hydrolase is a lipase from bacteria of *Burkholderia plantarii*.

18. The process of claim 16, wherein the hydrolase is a lipase from bacteria of *Burkholderia cepacia*.

19. The process of claim 1, wherein the hydrolase is selected from the group consisting of a lipase from bacteria of *Burkholderia plantarii*, a lipase from bacteria of *Burkholderia cepacia*, a lipase from bacteria of *Pseudomonas stutzeri*, and a lipase from fungal strains of *Thermomyces lanugenosus*.

* * * * *